United States Patent
Inoue et al.

(10) Patent No.: US 10,281,415 B2
(45) Date of Patent: May 7, 2019

(54) PATTERN INSPECTION METHOD AND PATTERN INSPECTION APPARATUS

(71) Applicant: NuFlare Technology, Inc., Yokohama-shi (JP)

(72) Inventors: Takafumi Inoue, Chigasaki (JP); Nobutaka Kikuiri, Koganei (JP)

(73) Assignee: NuFlare Technology, Inc., Yokohama-shi (JP)

( * ) Notice: Subject to any disclaimer, the term of this patent is extended or adjusted under 35 U.S.C. 154(b) by 277 days.

(21) Appl. No.: 15/274,413

(22) Filed: Sep. 23, 2016

(65) Prior Publication Data
US 2017/0122890 A1    May 4, 2017

(30) Foreign Application Priority Data
Oct. 28, 2015  (JP) ................................. 2015-211998

(51) Int. Cl.
*H01J 37/28*    (2006.01)
*G01N 23/2251*    (2018.01)
(Continued)

(52) U.S. Cl.
CPC ......... *G01N 23/2251* (2013.01); *G06T 5/002* (2013.01); *G06T 7/001* (2013.01);
(Continued)

(58) Field of Classification Search
CPC ........... G06T 5/00; G06T 5/001; G06T 5/002; G06T 2207/10061; G06T 2207/30148;
(Continued)

(56) References Cited

U.S. PATENT DOCUMENTS 6,587,581 B1 * 7/2003 Matsuyama ....... G01N 21/8851
                                                                  250/305
6,614,923 B1 * 9/2003 Shishido ................. G06T 5/006
                                                                  382/144
(Continued)

FOREIGN PATENT DOCUMENTS

JP     11-194154 A     7/1999
JP     2011-155119    8/2011
JP     2012-211834 A  11/2012

OTHER PUBLICATIONS

Combined Taiwanese Office Action and Search Report dated Feb. 23, 2018 in Patent Application No. 105130851 (with English translation), 18 pages.
(Continued)

*Primary Examiner* — Geoffrey E Summers
(74) *Attorney, Agent, or Firm* — Oblon, McClelland, Maier & Neustadt, L.L.P.

(57) ABSTRACT

A pattern inspection method includes: scanning an inspection substrate, to be inspected, to detect a secondary electron group emitted from the inspection substrate due to irradiation with the multiple beams; correcting individually distortion of a first region image obtained from a detection signal of secondary electrons corresponding to a corresponding first region for each beam of the multiple beams; correcting distortion of a corresponding second region image corresponding to a second region larger than the first region for each of the second region images, using data of each of the first region images in which the distortion of the corresponding first region image has been corrected; and comparing an inspection image to be inspected, in which the distortion of each of the plurality of second region images has been corrected, with a reference image of a same region to output a result thereof.

10 Claims, 14 Drawing Sheets

(51) Int. Cl.
*G06T 7/00* (2017.01)
*G06T 5/00* (2006.01)
*H01J 37/22* (2006.01)

(52) U.S. Cl.
CPC ............ *H01J 37/222* (2013.01); *H01J 37/28* (2013.01); *G01N 2223/6116* (2013.01); *G06T 2207/10061* (2013.01); *G06T 2207/30148* (2013.01); *H01J 2237/2826* (2013.01)

(58) Field of Classification Search
CPC ..... G06T 7/0004; G06T 7/0008; G06T 7/001; H01J 37/28; H01J 37/222; H01J 2237/2826; G01N 23/2251; G01N 2223/6116
USPC ........ 382/254, 274, 275, 144, 145, 147, 149
See application file for complete search history.

(56) References Cited

U.S. PATENT DOCUMENTS

| | | | |
|---|---|---|---|
| 2006/0029286 A1* | 2/2006 | Lim | G01N 23/225 382/260 |
| 2014/0346350 A1* | 11/2014 | Luo | H01J 37/02 250/307 |
| 2016/0300689 A1* | 10/2016 | Tromp | H01J 37/222 |

OTHER PUBLICATIONS

Office Action dated Nov. 24, 2017 in Korean Patent Application No. 10-2016-0141939 (with English language translation).
Korean Office Action dated May 19, 2017 in Patent Application No. 10-2016-0141939 (with English translation).

* cited by examiner

PATTERN INSPECTION METHOD AND PATTERN INSPECTION APPARATUS

CROSS-REFERENCE TO RELATED APPLICATION

This application is based upon and claims the benefit of priority from prior Japanese Patent Application No. 2015-211998 filed on Oct. 28, 2015 in Japan, the entire contents of which are incorporated herein by reference.

BACKGROUND OF THE INVENTION

Field of the Invention

Embodiments described herein relate generally to a pattern inspection method and a pattern inspection apparatus. For example, Embodiments described herein relates to an inspection apparatus that inspects a pattern by acquiring a secondary electronic image of a pattern image emitted after irradiation with an electron beam.

Related Art

In recent years, with increasingly higher integration and larger capacities of large scale integrated circuits (LSI), circuit linewidths required of semiconductor devices become increasingly narrower. These semiconductor devices are manufactured by exposing and transferring a pattern onto a wafer through a reduction projection exposure apparatus called the so-called stepper using an original pattern (also called a mask or reticle. Hereinafter, generically called a mask) in which a circuit pattern is formed, to form a circuit. Thus, a pattern lithography apparatus capable of writing a fine circuit pattern and using an electron beam is used to manufacture masks to transfer such a fine circuit pattern to a wafer. Using such a pattern lithography apparatus, a pattern circuit may directly be written to a wafer. Alternatively, an attempt is being made to develop a laser beam lithography apparatus that writes a pattern using a laser beam other than the electron beam.

Improvements in yield are indispensable for the manufacture of LSI that needs a large amount of manufacturing costs. However, as representatively shown by 1 GB DRAM (random access memory), patterns constituting LSI are transitioning from the order of sub micrometer to that of nanometer. Pattern defects of a mask to expose and transfer a superfine pattern onto a semiconductor wafer by photolithography technology can be cited as one important factor that reduces yields In recent years, with increasingly finer dimensions of LSI patterns formed on semiconductor wafers, dimensions that need to be detected as pattern defects are now extremely small. Therefore, a pattern inspection apparatus that inspects for defects of transfer masks used for the manufacture of LSI needs to be more precise.

As an inspection method, a method of conducting inspection by comparing an optical image capturing a pattern in a predetermined magnification formed on a substrate such as a lithography mask using an enlarged optical system and an optical image of design data or capturing the same pattern of a target object is known. For example, "die to die inspection" that compares optical image data capturing the same pattern in different places on the same mask and "die to database inspection" that, when writing pattern-designed CAD data to a mask as a pattern, inputs pattern writing data (design pattern data) converted into an apparatus input format for a lithography apparatus to input into an inspection apparatus, generates design image data (reference image) based thereon, and compares this data with an optical image as measurement data imaging the pattern are available as the pattern inspection method. In an inspection method in such an inspection apparatus, a target object is placed on a stage and the stage is moved for a luminous flux to scan the target object to conduct inspection. The target object is irradiated with a luminous flux by a light source and an illuminating optical system. Light transmitted or reflected by a target object is formed as an image on a sensor via an optical system. An image captured by the sensor is sent to a comparator as measurement data. After images are aligned, the comparator compares the measurement data and reference data using an appropriate algorithm and if not matched, determines that there are pattern defects.

In the above pattern inspection apparatus, a substrate is irradiated with laser light and a transmitted image or a reflected image thereof is captured to acquire an optical image. On the other hand, an inspection apparatus that acquires a pattern image by irradiating a substrate with multiple beams based on an electron beam and detecting secondary electrons corresponding to each beam emitted from the substrate is also under development (see, for example, JP-A-2011-155119). In the pattern inspection apparatus using multiple beams, a secondary electronic image obtained from the whole multiple beams is compared with a reference image. At this point, if individual distortions or gradation errors resulting from each beam constituting multiple beams arise, dummy defects determined to be defects, though not originally defects, may arise. However, it is difficult to individually correct beam characteristics or the like of each beam constituting multiple beams. In addition, even if an image obtained from the whole multiple beams is corrected, it is difficult to exclude such individual distortions or gradation errors. Countermeasures against such phenomena specific to multiple beams have not sufficiently been taken.

BRIEF SUMMARY OF THE INVENTION

According to one aspect of the present invention, a pattern inspection method includes: scanning an inspection substrate, to be inspected, on which a plurality of figures is formed using multiple beams in which a plurality of electron beams is arranged with a predetermined pitch to detect a secondary electron group including reflected electrons emitted from the inspection substrate due to irradiation with the multiple beams; correcting individually distortion of a corresponding first region image of a plurality of first region images each obtained from a detection signal of secondary electrons corresponding to a corresponding first region of a plurality of first regions on the inspection substrate, the plurality of first regions each scanned by a corresponding beam of the multiple beams, for each beam of the multiple beams; correcting distortion of a corresponding second region image of a plurality of second region images corresponding to a plurality of second regions each larger than the first region for each of the plurality of second region images, using data of each of the plurality of first region images in which the distortion of the corresponding first region image has been corrected individually for the each beam; and comparing an inspection image of a plurality of inspection images to be inspected, each having the plurality of second region images and in which the distortion of each of the plurality of second region images has been corrected, with a reference image of a same region as that of the inspection image to output a result thereof.

According to another aspect of the present invention, a pattern inspection apparatus includes: a movable stage on which an inspection substrate, to be inspected, on which a plurality of figures is formed is placed; an electron beam column configured to irradiate the inspection substrate with multiple beams in which a plurality of electron beams is arranged with a predetermined pitch; a detector configured to scan the inspection substrate using the multiple beams and to detect a secondary electron group including reflected electrons emitted from the inspection substrate due to irradiation with the multiple beams; first correction processing circuitry configured to correct individually distortion of a corresponding first region image of a plurality of first region images each obtained from a detection signal of secondary electrons corresponding to a corresponding first region of a plurality of first regions on the inspection substrate, the plurality of first regions each scanned by a corresponding beam of the multiple beams, for each beam of the multiple beams; second correction processing circuitry configured to correct distortion of a corresponding second region image of a plurality of second region images corresponding to a plurality of second regions each larger than the first region for each of the plurality of second region images, using data of each of the plurality of first region images in which the distortion of the corresponding first region image has been corrected individually for the each beam; and comparison processing circuitry configured to compare an inspection image of a plurality of inspection images to be inspected, each having the plurality of second region images and in which the distortion of each of the plurality of second region images has been corrected, with a reference image of a same region as that of the inspection image.

DETAILED DESCRIPTION OF THE INVENTION

Embodiment 1

Hereinafter, in Embodiment 1, a pattern inspection apparatus and method capable of reducing dummy defects specific to multiple-beam inspection in pattern inspection using multiple beams based on an electron beam.

Figure 1:
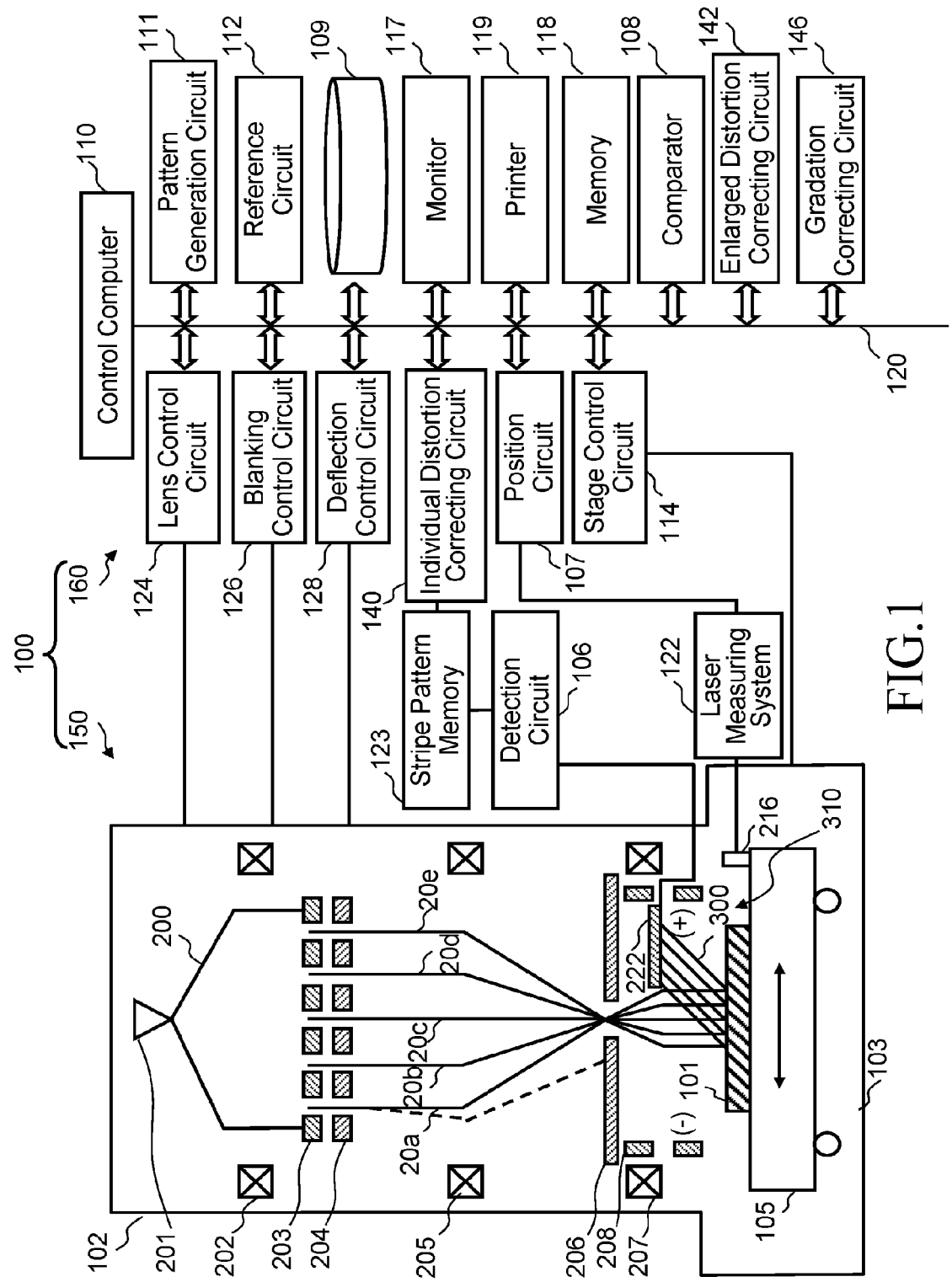
FIG. 1 is a block diagram showing the configuration of a pattern inspection apparatus according to Embodiment 1.

FIG. 1 is a block diagram showing the configuration of a pattern inspection apparatus according to Embodiment 1; In FIG. 1, an inspection apparatus 100 that inspects a pattern formed on a substrate is an example of a multi-electron beam inspection apparatus. The inspection apparatus 100 includes a secondary electronic image acquiring mechanism 150 and a control system circuit 160 (controller). The secondary electronic image acquiring mechanism 150 includes an electron beam column 102 (electron optical column), an inspection chamber 103, a detection circuit 106, a stripe pattern memory 123, and a laser measuring system 122. Inside the electron beam column 102, an electron gun assembly 201, an illumination lens 202, a shaping aperture array substrate 203, a blanking aperture array mechanism 204, a reducing lens 205, a limiting aperture plate member 206, an objective lens 207, a deflector 208, a deflector 224, and a detector 222 are arranged.

Inside the inspection chamber 103, an XY stage 105 capable of moving at least in the X and Y directions is arranged. A substrate 101 on which a plurality of figures to be inspected is formed is arranged on the XY stage 105. The substrate 101 includes, as described above, a mask for exposure, and a semiconductor substrate such as a silicon wafer. The substrate 101 is arranged on the XY stage 105 with, for example, a pattern forming surface directed upward. Also, a mirror 216 that reflects laser light for laser measurement emitted from the laser measuring system 122 arranged outside the inspection chamber 103 is arranged on the XY stage 105. The detector 222 is connected to the detection circuit 106 outside the electron beam column 102. The detection circuit 106 is connected to the stripe pattern memory 123.

In the control system circuit 160, a control computer 110 as a computer is connected to a position circuit 107, a comparator 108, a pattern generation circuit 111, a reference circuit 112, a stage control circuit 114, a lens control circuit 124, a blanking control circuit 126, a deflection control circuit 128, an individual distortion correcting circuit 140, an enlarged distortion correcting circuit 142, a gradation correcting circuit 146, a storage apparatus 109 such as a magnetic disk drive, a monitor 117, a memory 118, and a printer 119 via a bus 120. The stripe pattern memory 123 is connected to the individual distortion correcting circuit 140. The XY stage 105 is driven by the stage control circuit 114 under the control of the control computer 110. The XY stage 105 is movable by a drive system like a triaxial (X–Y–θ) motor driving in the X, Y, and θ directions. As an X motor, a Y motor, and a θ motor (not shown) of the drive system, for example, a step motor can be used. The XY stage 105 is movable by the motor of each of X, Y, and θ axes in the horizontal direction and the rotation direction. Then, the position of movement of the XY stage 105 is measured by the laser measuring system 122 and supplied to the position circuit 107. The laser measuring system 122 measures the position of the XY stage 105 by receiving reflected light from the mirror 216 and applying the principle of laser interferometry.

A high-voltage power circuit (not shown) is connected to the electron gun assembly 201 and an electron group emitted from a cathode is accelerated and emitted as an electron beam by applying a predetermined bias voltage and heating a cathode at a predetermined temperature in addition to applying an acceleration voltage from the high-voltage power circuit to between the cathode and an anode (not shown) inside the electron gun assembly 201. For example, an electron lens is used as the illumination lens 202, the reducing lens 205, and the objective lens 207 and all lenses are controlled by the lens control circuit 124. As described below, a plurality of individual blanking mechanisms is arranged in the blanking aperture array mechanism 204 and a control signal to each individual blanking mechanism is output from the blanking control circuit 126. The deflector 208 is constituted by an electrode group of at least four electrodes and controlled by the deflection control circuit 128. The deflector 224 is constituted by an electrode group of at least two electrodes and controlled by the deflection control circuit 128.

If the substrate 101 is a mask for exposure, when a plurality of figures is formed on the mask for exposure by, for example, a lithography apparatus (not shown) such as an electron beam lithography apparatus, pattern writing data used by the lithography apparatus is input from outside an inspection apparatus 500 and stored in the storage apparatus 109. If the substrate 101 is a semiconductor substrate, exposure image data defining an exposure image on the substrate when a mask pattern of the mask for exposure is exposed and transferred to the semiconductor substrate is input from outside the inspection apparatus 500 and stored in the storage apparatus 109. The exposure image data may be created by, for example, a spatial image capturing apparatus.

Here, in FIG. 1, only the configuration needed to describe Embodiment 1 is shown. Other configurations normally needed for the inspection apparatus 100 may also be included.

Figure 2:
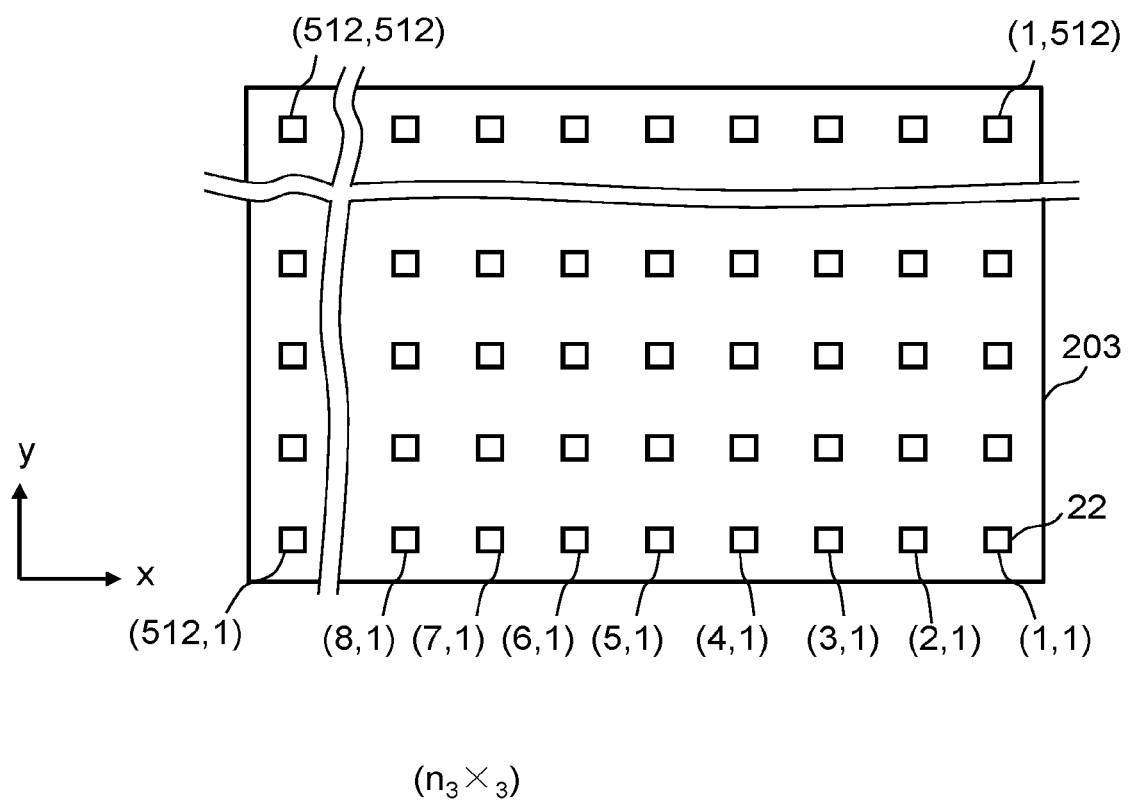
FIG. 2 is a conceptual diagram showing the configuration of a shaping aperture array substrate according to Embodiment 1.

FIG. 2 is a conceptual diagram showing the configuration of a shaping aperture array substrate according to Embodiment 1; In FIG. 2, the shaping aperture array substrate 203 has holes (openings) 22 of two-dimensional $n_3$ rows wide (x direction)×$m_3$ rows high (y direction) (one of $n_3$, $m_3$ is an integer equal to 1 or greater and the other is an integer equal to 2 or greater) formed with predetermined arrangement pitches in a matrix of rows and columns. In FIG. 2, for example, the holes 22 of 512×512 rows are formed horizontally or vertically (x, y directions). Each of the holes 22 is formed in a rectangular shape of the same dimensions. Alternatively, each of the holes 22 may be formed in a circular shape of the same outside diameter. Multiple beams 20 are formed by a portion of an electron beam 200 being passed through a plurality of these holes 22. Here, an example in which the holes 22 of two rows or more are arranged both horizontally or vertically (x, y directions) is shown, but the present embodiment is not limited to such an example. For example, a plurality of rows may be arranged horizontally or vertically (x or y direction) and only one row may be arranged in the other direction. Also, the method of arranging the holes 22 is not limited to a case of arranging holes in a grid-like shape like in FIG. 9. For example, the holes in the k-th row and the (k+1)-th row in the vertical direction (y direction) may be arranged by being shifted by a dimension a in the horizontal direction (x direction) from each other. Similarly, the holes in the (k+1)-th row and the (k+2)-th row in the vertical direction (y direction) may be arranged by being shifted by a dimension b in the horizontal direction (x direction) from each other.

Figure 3:
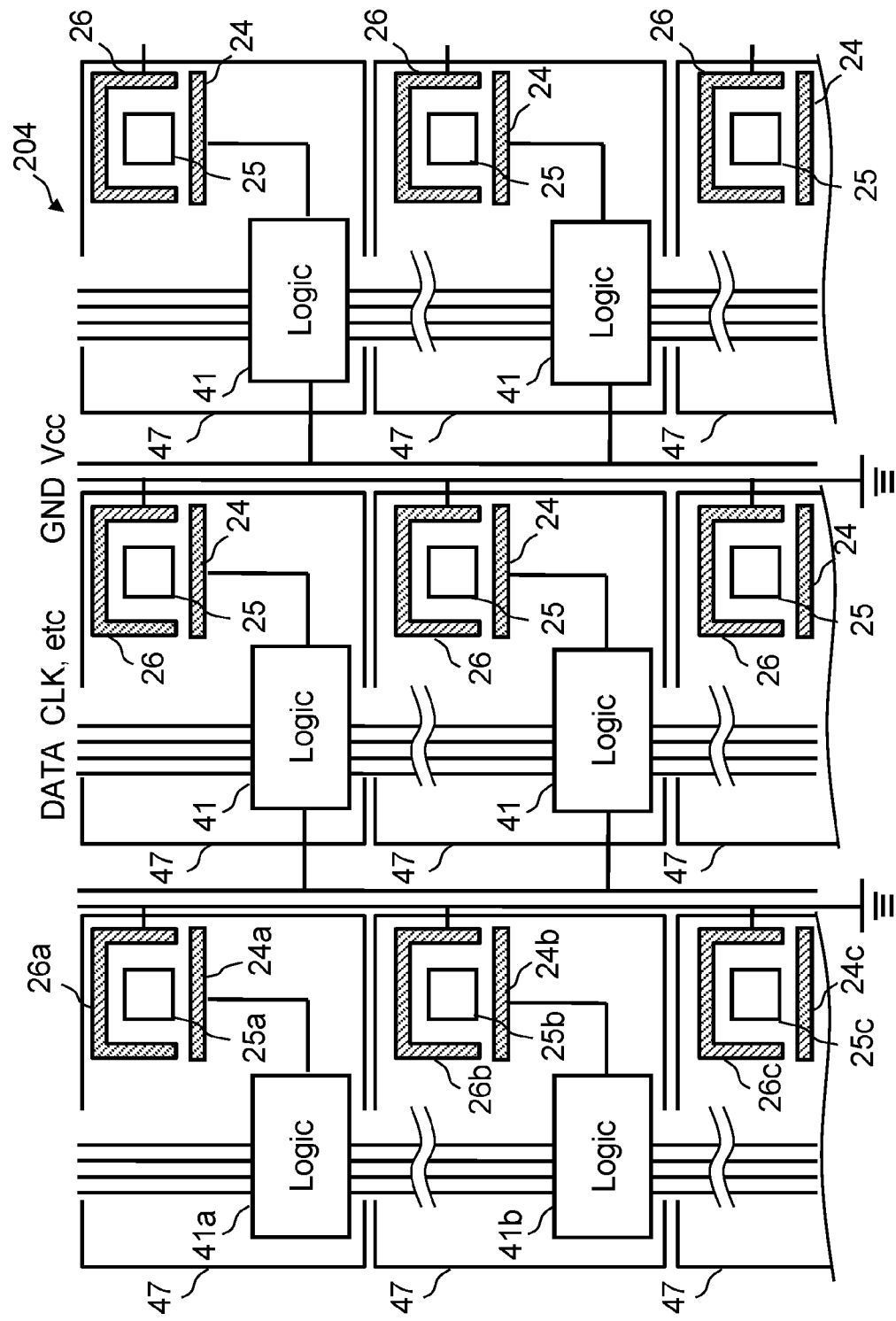
FIG. 3 is a top conceptual diagram showing a portion of a blanking aperture array mechanism according to Embodiment 1.

FIG. 3 is a top conceptual diagram showing a portion of a blanking aperture array mechanism according to Embodiment 1; In FIG. 3, the physical relationship among electrodes 24, 26, and a control circuit 41 does not correspond to the actual physical relationship. The blanking aperture array mechanism 204 has, as shown in FIG. 3, a passing hole 25 (opening) for passing each beam of multiple beams opened in a position corresponding to each of the holes 22 of the shaping aperture array substrate 203 shown in FIG. 2. Then, a pair (blanker: blanking deflector) of the electrodes 24, 26 for blanking deflection is arranged in a neighborhood position of each of the passing holes 25 across a relevant passing hole 25. Also, the control circuit 41 (logic circuit) that applies a deflecting voltage to, for example, the electrode 24 for each of the passing holes 25 is arranged in the neighborhood of each of the passing holes 25. The other (for example, the electrode 26) of the two electrodes 24, 26 for each beam is connected to the ground. Also, for example, a 1-bit wire for control signal is connected to each of the control circuits 41. In addition to, for example, the 1-bit wire, a clock signal line and a power wire respectively are connected to each of the control circuits 41. An individual blanking mechanism 47 is configured for each beam constituting multiple beams by the electrodes 24, 26 and the control circuit 41. A control signal for each of the control circuits 41 is output from a blanking control circuit 526. Shift registers (not shown) are arranged in each of the control circuits 41 and, for example, shift registers inside the control circuit for one row of $n_3 \times m_3$ multiple beams are connected in series. Then, for example, control signals for one row of $n_3 \times m_3$ multiple beams are transmitted in series and the control signal of each beam is stored in a corresponding control circuit 41 by, for example, $n_3$ clock signals.

The electron beam 20 passing through each passing hole is deflected by the voltage applied independently to the two electrodes 24, 26 forming a pair. Blanking control is exercised by such deflection. The corresponding beam of multiple beams is each deflected by blanking. Thus, a plurality of blankers deflects by blanking a corresponding beam of multiple beams having passed through a plurality of the holes 22 (openings) of the shaping aperture array substrate 203.

Next, the operation of an optical image acquiring unit 550 in the inspection apparatus 100 will be described. The electron beam 200 emitted from the electron gun assembly 201 (emitting unit) illuminates the entire shaping aperture array substrate 203 almost vertically through the illumination lens 202. The shaping aperture array substrate 203 has a plurality of rectangular holes (openings) formed therein and the electron beam 200 illuminates a region including all the plurality of holes. A plurality of electron beams (multiple beams) 20a to 20e in, for example, a rectangular shape is formed by a portion of each of the electron beams 200 with which the positions of the plurality of holes are irradiated being passed through each of the plurality of holes of the shaping aperture array substrate 203. The multiple beams 20a to 20e pass through the respective corresponding blankers (first deflector: individual blanking mechanism) of the blanking aperture array mechanism 204. Such blankers individually deflect (deflect by blanking) the passing electron beam 20.

The multiple beams 20a to 20e having passed through the blanking aperture array mechanism 204 are reduced by the reducing lens 205 before traveling toward a hole in the center formed in the limiting aperture plate member 206. Here, the electron beam 20 deflected by the blanker of the blanking aperture array mechanism 204 deviates from the position of the hole in the center of the limiting aperture plate member 206 and is shielded by the limiting aperture plate member 206. On the other hand, the electron beam 20 that is not deflected by the blanker of the blanking aperture array mechanism 204 passes, as shown in FIG. 1, through the hole in the center of the limiting aperture plate member 206. The blanking control is exercised by ON/OFF of the individual blanking mechanism to control ON/OFF of a beam. In this manner, the limiting aperture plate member 206 shields each beam deflected so as to be in a beam OFF state by the individual blanking mechanism. Then, a beam for one shot is formed for each beam by a beam formed between beam ON and beam OFF and having passed through the limiting aperture plate member 206. The multiple beams 20 having passed through the limiting aperture plate member 206 are focused by the objective lens 207 to become a pattern image of a desired reduction ratio and each beam (multiple beams 20 as a whole) having passed through the limiting aperture plate member 206 is deflected collectively in the same direction by the deflector 208 and targeted at the irradiation position of each beam on the substrate 101. The multiple beams 20 emitted at a time are ideally arranged with pitches obtained by multiplying the arrangement pitch of the plurality of holes of the shaping aperture array substrate 203 by the above desired reduction ratio. In this manner, the electron beam column 102 irradiates the substrate 101 with two-dimensional $n_3 \times m_3$ multiple beams 20 at a time. A secondary electron group 310 as a bundle of secondary electrons 300 including reflected electrons corresponding to each beam of the multiple beams 20 emitted from the substrate 101 due to irradiation of a desired position of the substrate 101 with the multiple beams 20 is deflected by the deflector 224 to the side of the detector 222 and detected by being input into the detector 222. The secondary electron group 310 has kinetic energy smaller than that of the multiple beams 20 for irradiation. Thus, the deflector 224 can deflect only the secondary electron group 310 having kinetic energy smaller than that of the multiple beams 20 for irradiation without deflecting the multiple beams 20 for irradiation accelerated by a large acceleration voltage by causing a weak electric field.

Figure 4:
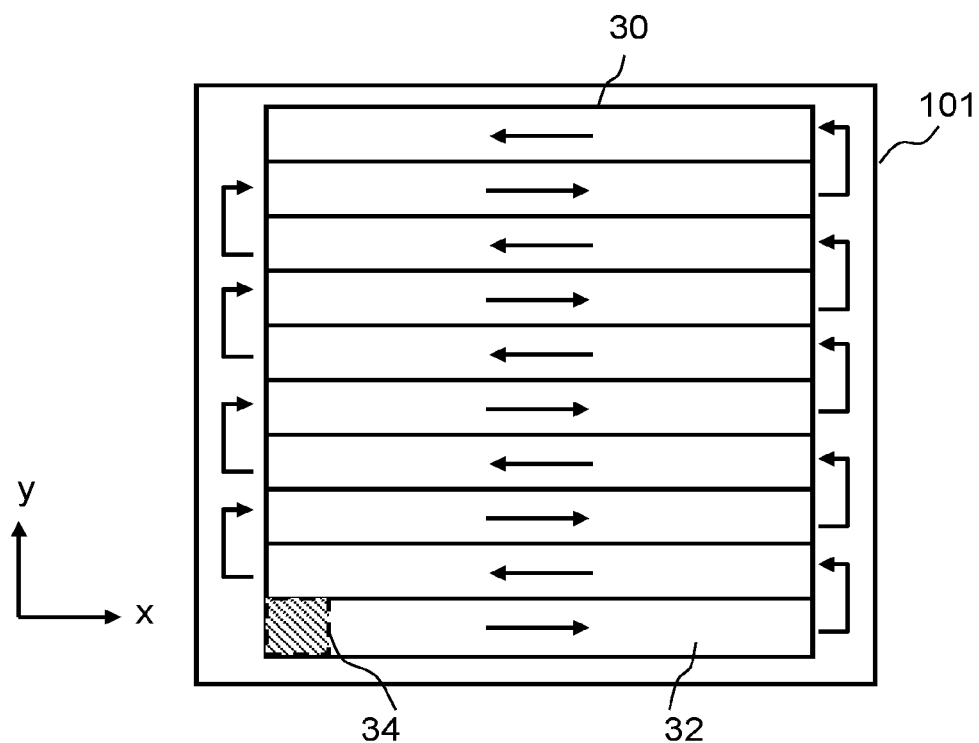
FIG. 4 is a conceptual diagram illustrating an example of a scan operation according to Embodiment 1.

FIG. 4 is a conceptual diagram illustrating an example of a scan operation according to Embodiment 1; As shown in FIG. 4, an inspection region 30 of the substrate 101 is virtually divided, for example, into a plurality of stripe regions 32 in a thin rectangular shape of a predetermined width in the y direction. For example, the inspection region 30 is virtually divided into the plurality of stripe regions 32 in a thin rectangular shape of the same width as that of an irradiation region 34 that can be irradiated with the multiple beams 20 as a whole at a time. First, the XY stage 105 is moved to adjust such that the irradiation region 34 that can be irradiated with the multiple beams 20 at a time is positioned on the left end of the first stripe region 32 or in a position further to the left before a scan operation being started. In Embodiment 1, the irradiation region 34 is scanned while the irradiation region 34 is sequentially shifted by the width of the irradiation region 34 in the x direction by repeating, for example, a step and repeat operation. When the first stripe region 32 is scanned, the XY stage 105 is moved in, for example, the −x direction to proceed with the scan operation relatively in the x direction. When the irradiation of the first stripe region 32 with multiple beams for inspection is finished, the stage position is moved in the −y direction to adjust such that the irradiation region 34 is positioned on the right end of the second stripe region 32 or in a position further to the right relatively in the y direction, and this time, the XY stage 105 is moved in, for example, the x direction for irradiation with multiple beams in the same manner toward the −x direction. The inspection time can be shortened by alternately changing the scanning direction like multiple beam irradiation toward the x direction in the third stripe region 32 and multiple beam irradiation toward the −x direction in the fourth stripe region 32. However, the present embodiment is not limited to a case of alternately changing the scanning direction and when a pattern is written to each of the stripe regions 32, a scan may be performed in the same direction. In a shot, the secondary electron group 310 of a bundle of secondary electrons in accordance with maximally a plurality of shots as many as the number of the holes 22 is detected at a time by multiple beams formed by passing through each of the holes 22 of the shaping aperture array substrate 203.

Figure 5:
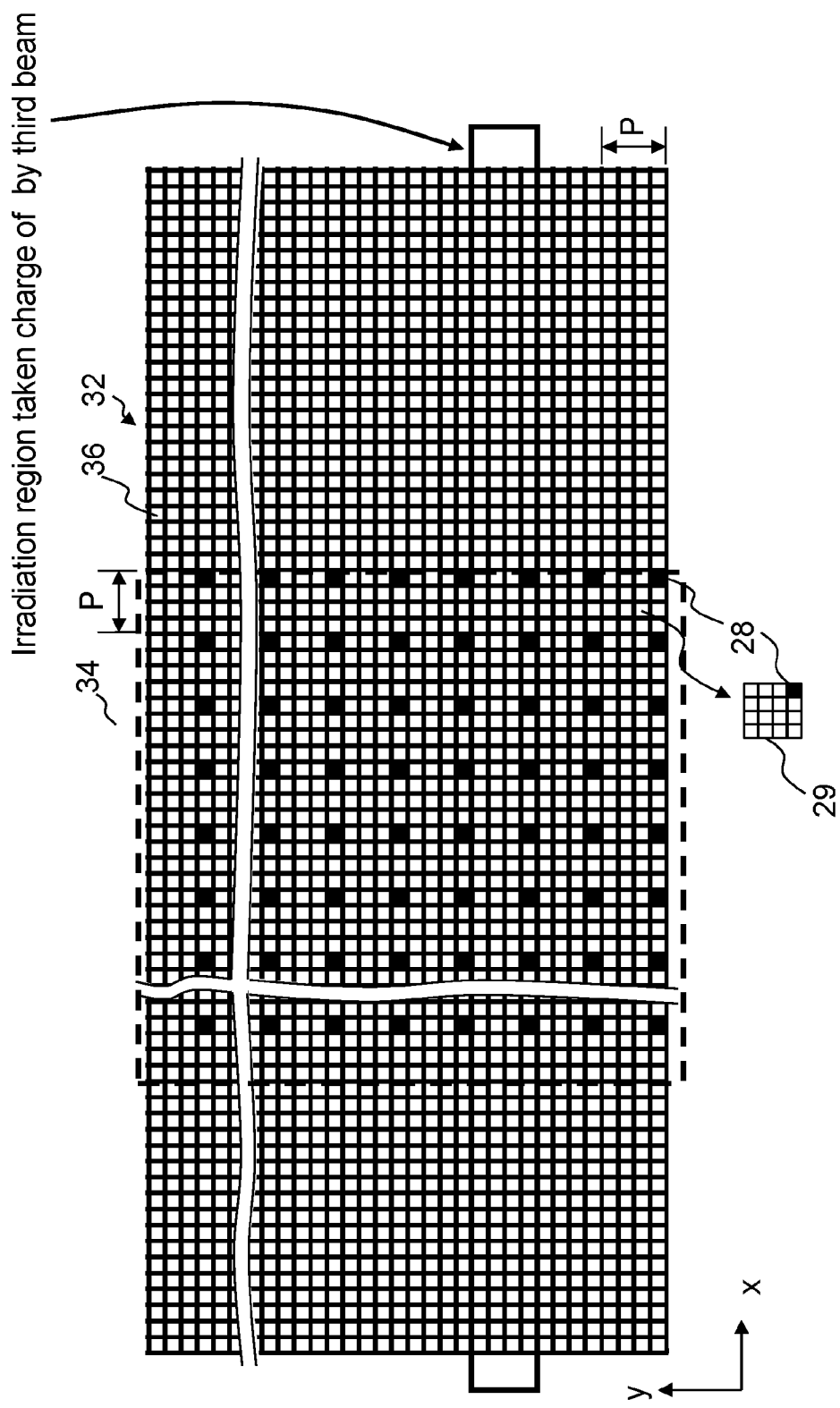
FIG. 5 is a diagram showing an example of an irradiation region and pixels for measurement of multiple beams according to Embodiment 1.

FIG. 5 is a diagram showing an example of an irradiation region and pixels for measurement of multiple beams according to Embodiment 1; In FIG. 5, the stripe region 32 is divided into, for example, a plurality of mesh regions in a mesh shape of the beam size of multiple beams. Each such mesh region becomes a pixel for measurement 36 (unit irradiation region). In the example of FIG. 5, a case of dividing the inspection region of the substrate 101 into a plurality of the stripe regions 32 of the width size substantially the same as the size the irradiation region 34 (pattern writing field) that can be irradiated with the multiple beams 20 at a time in, for example, the y direction. However, the width of the stripe region 32 is not limited to the above example. The size thereof is suitably $n_4$ ($n_4$ is an integer equal to 1 or greater) times the irradiation region 34. In the example of FIG. 5, a case of multiple beams of 512×512 rows is shown. Then, a plurality of pixels for measurement 28 (irradiation position of beams for one shot) that can be irradiated with the multiple beams 20 at a time is shown inside the irradiation region 34. In other words, the pitch between the pixels for measurement 28 adjacent to each other becomes the pitch between beams of multiple beams. In the example of FIG. 5, a square region surrounded by the four pixels for measurement 28 adjacent to each other and containing the one pixels for measurement 28 of the four pixels for measurement 28 constitutes a grid 29. In the example of FIG. 5, a case in which each of the grids 29 is constituted by 4×4 pixels is shown.

Figure 6:
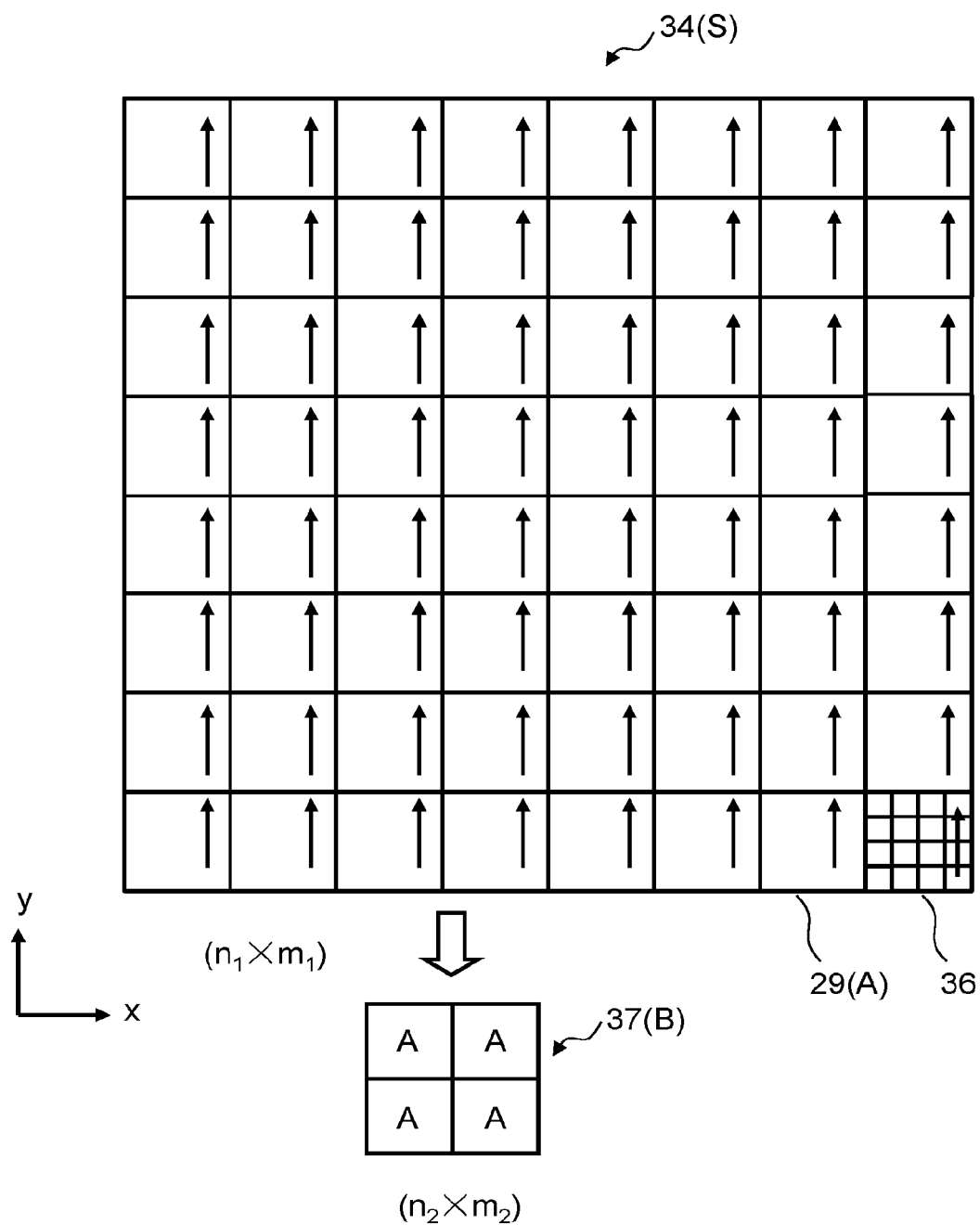
FIG. 6 is a conceptual diagram illustrating an example of details of the scan operation according to Embodiment 1.

FIG. 6 is a conceptual diagram illustrating an example of details of the scan operation according to Embodiment 1; In FIG. 6, an example of a case of scanning a certain irradiation region 34 is shown. The $n_1 \times m_1$ grids 29 are arranged in the x and y directions (two-dimensionally) inside the one irradiation region 34. When the XY stage 105 is moved to a position where the one irradiation region 34 can be irradiated with the multiple beams 20, the XY stage 105 is stopped in the position and a scan (scan operation) of the irradiation region 34 is performed. Each beam constituting the multiple beams 20 is in charge of one of the grids 29 different from each other. Then, the one pixel for measurement 28 corresponding to the same position inside the grid 29 in charge is irradiated with each beam during each shot. In the example of FIG. 6, a pixel for measurement 36 positioned rightmost in the lowest tier inside the grid 29 in charge is irradiated with each beam in the first shot. Then, the deflection position of the multiple beams 20 as a whole is collectively shifted by the deflector 208 by the one pixel for measurement 36 in the y direction to irradiate the pixel for measurement 36 rightmost in the second lowest tier inside the grid 29 in charge with each beam in the second shot. Similarly, the pixel for measurement 36 positioned rightmost in the third lowest tier inside the grid 29 in charge is irradiated with each beam in the third shot. The pixel for measurement 36 positioned rightmost in the fourth lowest tier inside the grid 29 in charge is irradiated with each beam in the fourth shot. Next, the deflection position of the multiple beams 20 as a whole is collectively shifted by the deflector 208 to the pixel for measurement 36 positioned second rightmost in the lowest tier to similarly irradiate the pixel for measurement 36 sequentially with each beam in the y direction. By repeating the above operation, all the pixels for measurement 36 inside the one grid 29 are sequentially irradiated with one beam.

While the multiple beams 20 as a whole scan the irradiation region 34 as described above, each beam scans the respective corresponding grid 29. Then, when the scan of the one irradiation region 34 is finished, the next neighboring irradiation region 34 is scanned. By repeating the above operation, each of the stripe regions 32 is scanned. The secondary electron group 310 is emitted from the pixel for measurement 36 irradiated after each shot of the multiple beams 20 and detected by the detector 222.

Detection data of the secondary electrons 300 from each of the pixels for measurement 36 detected by a detector 422 as described above is output to the detection circuit 106 in the order of measurement. Inside the detection circuit 106, analog detection data is converted into digital data by an A/D converter (not shown) and stored in the stripe pattern memory 123. Then, when detection data for the one stripe region 32 is stored, the data is transferred to the individual distortion correcting circuit 140 as stripe pattern data. Alternatively, when detection data for the one irradiation region 34 is stored, the data may be transferred to the individual distortion correcting circuit 140 as irradiation region pattern data.

By performing a scan using the multiple beams 20 as described above, a scan operation (measurement) can be performed faster than when a scan is performed using a single beam.

Figure 7:
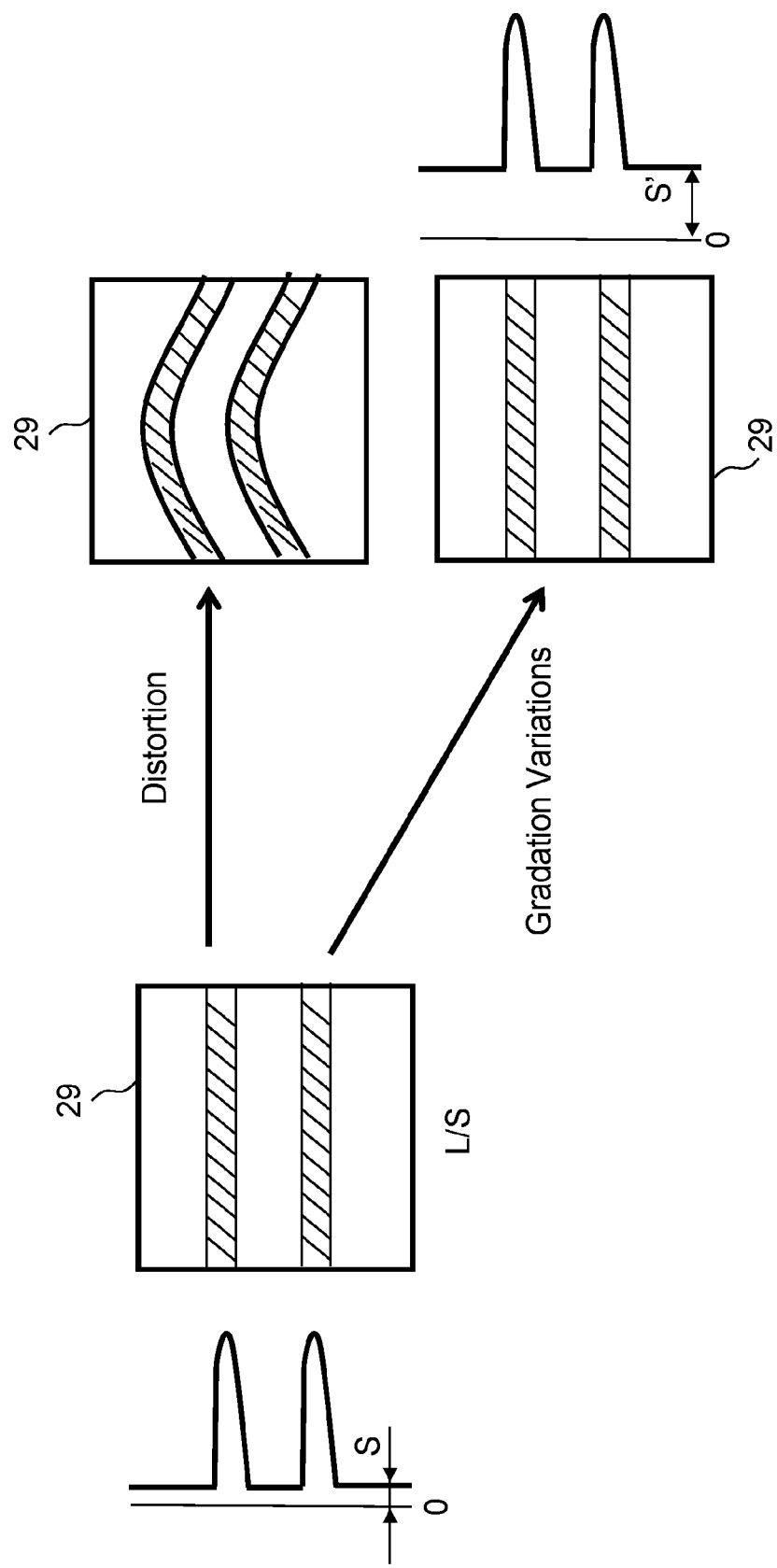
FIG. 7 is a diagram illustrating a distortion and a gradation error according to Embodiment 1.

FIG. 7 is a diagram illustrating a distortion and a gradation error according to Embodiment 1; The secondary electrons 300 from each of the pixels for measurement 36 are detected for each of the grid 29 by scanning of each beam inside the one irradiation region 34. Thus, an image is obtained for each of the grids 29 from detection data of each of the pixels for measurement 36 in the grid 29. However, because the beam to be used is different for each of the grids 29, as shown in FIG. 7, variations in distortion and variations of gradation errors due to gradation variations (from S to S') arise in grid images obtained for each of the grids 29. As will be described below, pattern inspection is performed for each of the irradiation regions 34. Each of the irradiation regions 34 includes a plurality of the grids 29 and thus, if variations in distortion or variations of gradation errors arise among grid images, a defect may be determined to be a dummy defect though the defect is originally not a defect. Therefore, dummy defects specific to multiple-beam inspection may arise in pattern inspection using the multiple beams 20.

Here, if distortion or gradation errors in an image are corrected in units of the grid 29 (A region unit), distortion or gradation errors remain in an image in units of the irradiation region 34 (S region unit). Conversely, if distortion or gradation errors in an image are corrected in units of the irradiation region 34 (S region unit), it is difficult to sufficiently correct errors specific to each beam. Thus, in Embodiment 1, distortion in an image is corrected in units of the grid 29 (A region unit) and then, correction residuals of the distortion are corrected in units of a region (B region unit) larger than the unit of the grid 29 (A region unit). By making such corrections, gradation errors are corrected in units of the region (B region unit) larger than the unit of the grid 29 (A region unit) after the pattern position is changed. By making corrections of a plurality of tires in units of a plurality of regions having different region sizes as described above, an image can be corrected to a more precise image.

Figure 8:
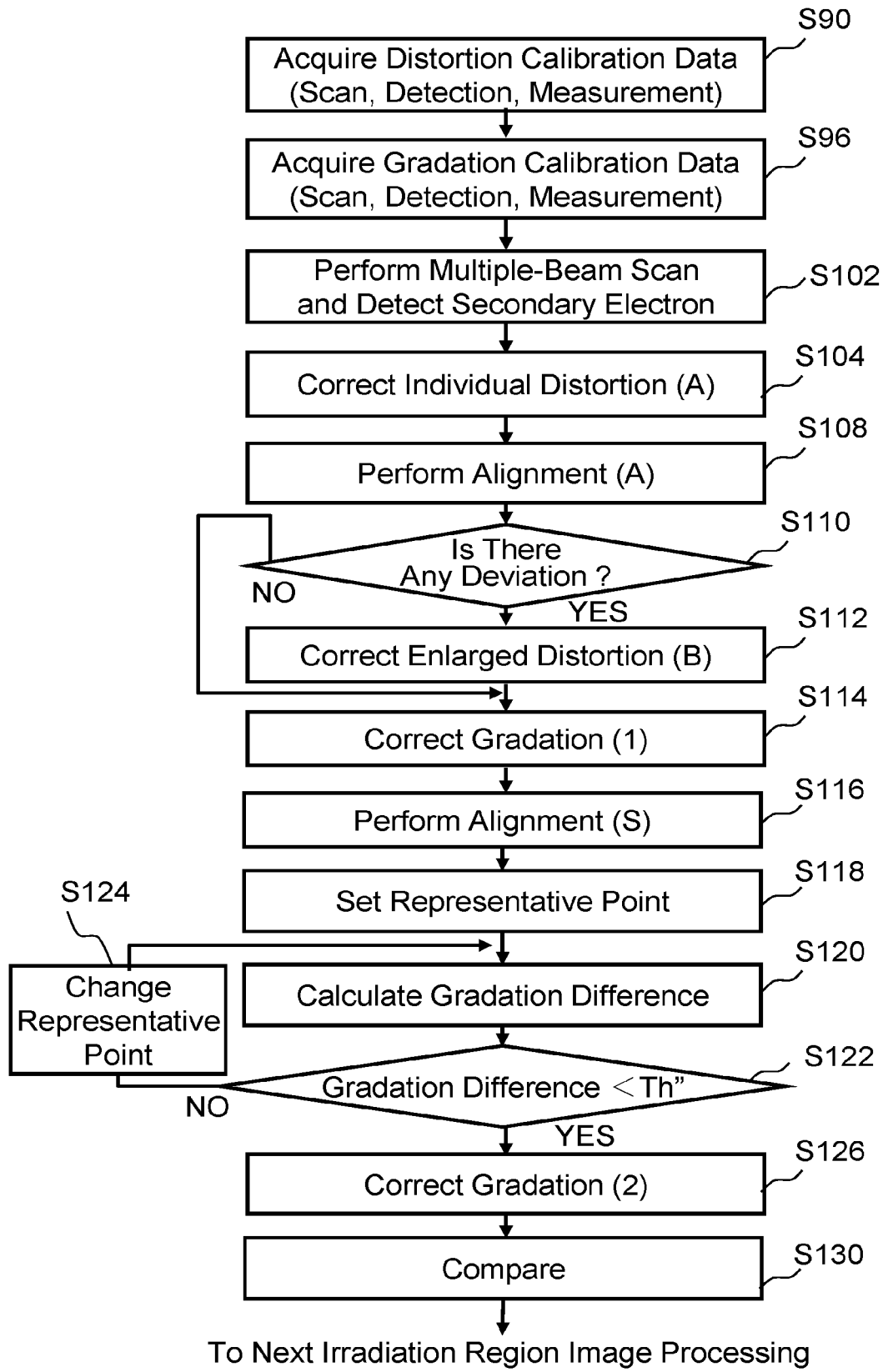
FIG. 8 is a flow chart showing principal processes of a pattern inspection method according to Embodiment 1.

FIG. 8 is a flow chart showing principal processes of a pattern inspection method according to Embodiment 1; In FIG. 8, the pattern inspection method according to Embodiment 1 performs a series of processes including a distortion calibration data acquisition process (S90), a gradation calibration data acquisition process (S96), a multiple-beam scan and secondary electron detection process (S102), an individual distortion correction process (S104), an alignment process (S108), a determination process (S110), an enlarged distortion correction process (S112), a gradation correction (1) process (S114), an alignment process (S116), a representative point setting process (S118), a gradation difference operation process (S120), a determination process (S122), a representative point change process (S124), a gradation correction (2) process (S126), and a comparison process (S130).

Data of the distortion calibration data acquisition process (S90) and the gradation calibration data acquisition process (S96) is acquired in advance before the inspection is conducted. Each process of the multiple-beam scan and secondary electron detection process (S102) and subsequent processes is performed for each of the irradiation regions 34.

As the distortion calibration data acquisition process (S90), distortion data for each of the grids 29 is measured using a calibration substrate. More specifically, measurements are made as described below.

Figure 9:
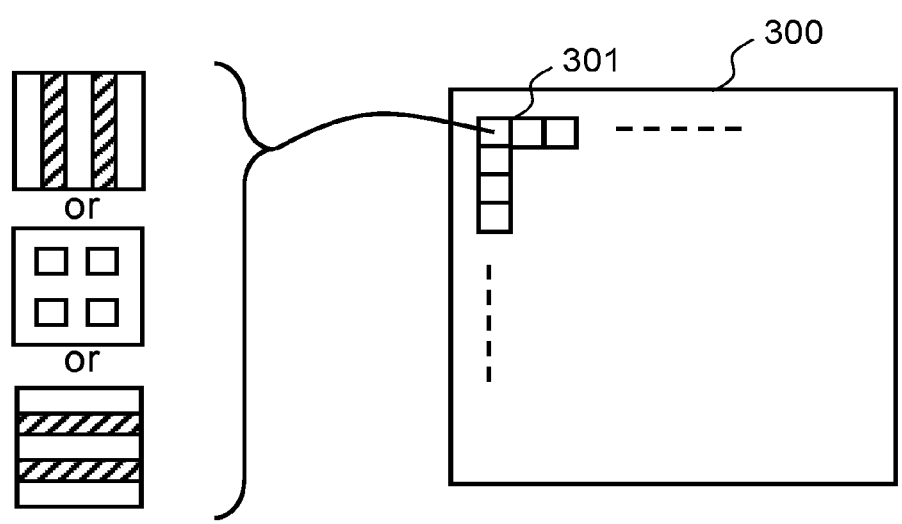
FIG. 9 is a diagram showing an example of a calibration substrate according to Embodiment 1.

FIG. 9 is a diagram showing an example of a calibration substrate according to Embodiment 1; In FIG. 9, at least one of a line and space pattern of the linewidth smaller than the size of the grid 29 arranged in the x direction, a line and space pattern of the linewidth smaller than the size of the grid 29 arranged in the y direction, and a plurality of rectangular patterns (for example, hole patterns) of the linewidth smaller than the size of the grid 29 is formed on a calibration substrate 300. These three patterns may be formed on the one calibration substrate 300 or separate calibration substrates. Hereinafter, a case in which three patterns are formed separate calibration substrates will be described. In FIG. 9, an image of each of grids 301 on the calibration substrate 300 of the same size as that of the grid 29 (first region) of the substrate 101 to be inspected is acquired.

First, the calibration substrate on which a calibration pattern is formed is scanned using the multiple beams 20 to detect a secondary electron group including reflected electrons emitted from the calibration substrate due to irradiation with the multiple beams 20. For example, a calibration substrate (1) on which a line and space pattern of the size smaller than that of the grid 29 arranged in the x direction is arranged in a region (for example, the inspection region 30 as a whole) larger than the irradiation region 34 is used and scanned using the multiple beams 20 in the same manner as described above to acquire secondary electron detection data of each of the grids 29.

Similarly, a calibration substrate (2) on which a line and space pattern of the size smaller than that of the grid 29 arranged in the y direction is arranged in a region (for example, the inspection region 30 as a whole) larger than the irradiation region 34 is used and scanned using the multiple beams 20 in the same manner as described above to acquire secondary electron detection data of each of the grids 29.

Similarly, a calibration substrate (3) on which a plurality of rectangular patterns (for example, hole patterns) of the size smaller than that of, for example, the grid 29 is arranged in a region (for example, the inspection region 30 as a whole) larger than the irradiation region 34 is used and scanned using the multiple beams 20 in the same manner as described above to acquire secondary electron detection data of each of the grids 29.

Next, the distortion amount of a grid image (third region image) obtained from a detection signal of secondary electrons corresponding to the grid 301 (third region) on the calibration substrate of the same size as that of the grid 29 (first region) scanned by each of the multiple beams 20 is individually measured for each beam. More specifically, the position of a line and space pattern formed on the calibration substrate (1) is measured using a position measuring apparatus (not shown). Then, a differential value obtained by subtracting the position of a pattern measured by the position measuring apparatus from the position of a pattern inside the obtained grid image (third region image) becomes a distortion amount of the line and space pattern arranged in the x direction in the grid 301. The value that corrects distortion of such an amount becomes distortion data of the line and space pattern arranged in the x direction.

Similarly, the position of a line and space pattern formed on the calibration substrate (2) is measured using the position measuring apparatus (not shown). Then, a differential value obtained by subtracting the position of a pattern measured by the position measuring apparatus from the position of a pattern inside the obtained grid image (third region image) becomes a distortion amount of the line and space pattern arranged in the y direction in the grid 301. The value that corrects distortion of such an amount becomes distortion data of the line and space pattern arranged in the y direction.

Similarly, the positions of a plurality of rectangular patterns formed on the calibration substrate (3) is measured using the position measuring apparatus (not shown). Then, a differential value obtained by subtracting the position of a pattern measured by the position measuring apparatus from the position of a pattern inside the grid image becomes a distortion amount of the rectangular patterns in the grid 301. The value that corrects distortion of such an amount becomes distortion data of the rectangular pattern. From the above, distortion data in each beam position specific to the multiple beams 20 can be acquired.

Then, a distortion data map defining the obtained distortion data in a mesh region of the corresponding position of a plurality of mesh regions adjusted to the size of the grid 301 (grid 29) is created. Thus, distortion data of the line and space pattern arranged in the x direction, distortion data of the line and space pattern arranged in the y direction, and distortion data of rectangular patterns are defined in one mesh region. The created distortion data map is input into the inspection apparatus 100 and stored in the storage apparatus 109.

As the gradation calibration data acquisition process (S96), the substrate 101 to be inspected is used to measure gradation value data of each of the grids 29. More specifically, measurements are made as described below.

First, a sample region of the size equal to that of the irradiation region 34 or more is scanned for each pattern type on the inspection substrate 101 using the multiple beams 20 to detect a secondary electron group including reflected electrons emitted from the inspection substrate 101 due to irradiation with the multiple beams 20. Patterns of at least one pattern type, normally a plurality of pattern types are formed on the inspection substrate 101. Then, normally patterns of the same pattern type are formed by being assembled in one place. In other words, the inspection region 30 of the inspection substrate 101 is generally divided by pattern type. Then, when the irradiation region 34 is set inside one pattern type, a secondary electron image of the irradiation region 34 generally becomes the same image if inside the same pattern type. In other words, the gradation value of the corresponding grid between the irradiation regions 34 generally takes the same value if inside the same pattern type. Thus, if a secondary electron image of the irradiation region 34 is obtained from a sample region of the size of the irradiation region 34 or more for each pattern type, the gradation value of each grid that should be obtained from inside the irradiation region 34 can be acquired for each pattern type. However, it is highly probable that an error is included after only one scan operation and thus, a secondary electron group after a plurality of scans is detected.

Then, the distortion amount of a grid image (third region image) obtained from a detection signal of secondary electrons corresponding to the grid (third region) in the sample region of the same size as that of the grid 29 (first region) scanned by each of the multiple beams 20 is individually measured for each beam and each pattern type. As described above, it is highly probable that an error is included after only one scan operation and thus, the average value of the gradation value of detection data for each grid of values obtained after a plurality of scans is used as gradation calibration data of each grid. From the above, for example, gradation calibration data of the line and space pattern arranged in the x direction, gradation calibration data of the line and space pattern arranged in the y direction, and gradation calibration data of the rectangular patterns are acquired.

Then, a gradation calibration data map defining the obtained gradation calibration data in a mesh region of the corresponding position of a plurality of mesh regions adjusted to the size of the grid 29 is created. Thus, gradation calibration data of the line and space pattern arranged in the x direction, gradation calibration data of the line and space pattern arranged in the y direction, and gradation calibration data of the rectangular patterns are defined for one mesh region. The created gradation calibration data map is input into the inspection apparatus 100 and stored in the storage apparatus 109.

After a distortion data map and a gradation calibration data map are created by making the above advance measurements, the inspection substrate 101 is inspected.

As the multiple-beam scan and secondary electron detection process (S102), the secondary electronic image acquiring mechanism 150 scans the inspection substrate 101 on which a plurality of figures is formed using the multiple beams 20 in which a plurality of electron beams is arranged with a predetermined pitch P and detects the secondary electron group 310 emitted from the inspection substrate 101 and including reflected electrons due to irradiation with the multiple beams 20. The method of scanning and the method of detecting the secondary electron group 310 are as described above. Detection data of the secondary electrons 300 from each of the pixels for measurement 36 detected by a detector 422 is output to the detection circuit 106 in the order of measurement. Inside the detection circuit 106, analog detection data is converted into digital data by an A/D converter (not shown) and stored in the stripe pattern memory 123. Then, when detection data for the one stripe region 32 is stored, the data is transferred to the individual distortion correcting circuit 140 as stripe pattern data. Alternatively, when detection data for the one irradiation region 34 is stored, the data may be transferred to the individual distortion correcting circuit 140 as irradiation region pattern data.

On the other hand, a reference image is created concurrently, or before or after the multiple-beam scan and secondary electron detection process (S102).

As the reference image creation process, if the substrate 101 is a mask for exposure, a reference image creator such as the pattern generation circuit 111 and the reference circuit 112 creates a reference image of a region corresponding to a measured image (optical image) of the grid 29 based on pattern writing data (design data) as a source to form a plurality of figures on the substrate 101. If the substrate 101 is a semiconductor substrate, the reference image creator such as the pattern generation circuit 111 and the reference circuit 112 creates a reference image of a region corresponding to a measured image (optical image) of the grid 29 based on exposure image data in which an exposure image on the substrate when a mask pattern of a mask for exposure is exposed and transferred to the semiconductor substrate is defined. Here, a plurality of reference images (design images) corresponding to a plurality of measured image regions 21 is created. A more specific operation is as described below. First, the pattern generation circuit 111 reads pattern writing data (or exposure image data) from the storage apparatus 109 through the control computer 110 and converts each figure of each of the irradiation regions 34 defined in the read pattern writing data (or the exposure image data) into binary or multivalued image data before sending the image data to the reference circuit 112.

Here, a figure defined in the pattern writing data (or the exposure image data) uses, for example, a rectangle and a triangle as basic figures and figure data defining the shape, size position and the like of each pattern is stored as information, for example, coordinates (x, y) in the reference position of the figure, lengths of sides, figure code to be an identifier to distinguish the figure type such as the rectangle and the triangle.

When pattern writing data (or exposure image data) to be such figure data is input into the pattern generation circuit 111, the pattern generation circuit 111 expands the pattern writing data up to data for each figure and interprets the figure code indicating the figure shape of the figure data, figure dimensions and the like. Then, the pattern generation circuit 111 expands and outputs binary or multivalued design image data as a pattern arranged inside a square using the grid of a predetermined quantization dimension as the unit. In other words, the pattern generation circuit 111 reads design data, calculates an occupancy rate occupied by figures in a design pattern for each square created by virtually dividing an inspection region into squares in units of a predetermined dimension, and outputs n-bit occupancy rate data. For example, one square is suitably set as one pixel. Then, if one pixel should have a resolution of $1/2^8$ ($=1/256$), the occupancy rate in the pixel is calculated by allocating small regions of $1/256$ to the regions of figures arranged in the pixel. Then, 8-bit occupancy rate data is output to the reference circuit 112. Such squares may have the same size as that of the pixel for measurement 36.

Next, the reference circuit 112 performs appropriate filter processing on the design image data as sent image data of figures. Measurement data as an optical image obtained from the detection circuit 106 is in a state in which filtering acts thereon by an electron optics, in other words, an analog state changing continuously and thus, the design image data as image data on the design side in which the image intensity (gray level) is a digital value can be adjusted to the measurement data by performing the filter processing also thereon. In this manner, a measured image (optical image) of the grid 29 to be compared with a design image (reference image) is created. Image data of the created reference image is output to the enlarged distortion correcting circuit 142 and the gradation correcting circuit 146 and the reference image output into the enlarged distortion correcting circuit 142 and the gradation correcting circuit 146 is stored in the respective memories.

In the way as described above, a plurality of reference images of a plurality of figures in accordance with a plurality of the grids 29 based on design data or the like in which the plurality of figures is defined for each of the plurality of grids 29 whose positions are different is created. Accordingly, the plurality of reference images corresponding to measured images of the plurality of grids 29 of each of the inspection stripes 32 detected from the substrate 101 is created.

As the individual distortion correction process (S104), the individual distortion correcting circuit 140 individually corrects distortion of a grid image (first region image) obtained from a detection signal of secondary electrons corresponding to the grid 29 (first region) scanned by each of the multiple beams 20 for each beam.

Figure 10:
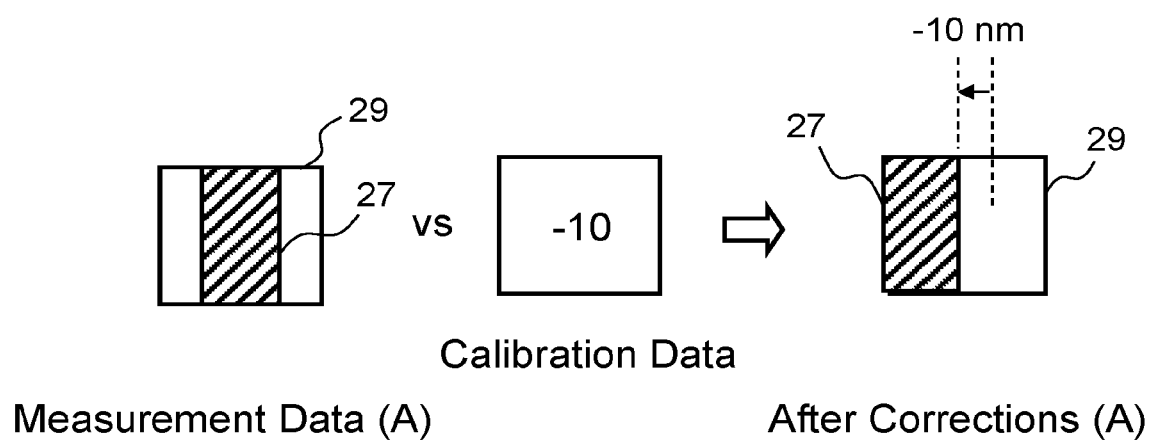
FIG. 10 is a diagram illustrating how to correct individual distortions according to Embodiment 1.

FIG. 10 is a diagram illustrating how to correct individual distortions according to Embodiment 1; The individual distortion correcting circuit 140 creates an image (grid image) of a pattern 27 inside the grid 29 from a detection signal of secondary electrons for each of the grids 29. The grid image (first region image) for each beam is corrected using the distortion amount of the corresponding grid image (third region image) on the measured calibration substrate. More specifically, the individual distortion correcting circuit 140 reads a distortion data map from the storage apparatus 109 and corrects the position of the image of the pattern 27 in the grid 29 only by the value of calibration data of the corresponding grid image (third region image) of the same pattern type on the distortion data map for each of the grids 29 (first region). In the example of FIG. 10, for example, if calibration data is "−10" in the x direction, the position of the pattern 27 in the relevant grid 29 is moved by −10 nm in the x direction. Accordingly, individual distortion corrections can be made for each of the grids 29. The pattern type in the relevant grid 29 may be determined using pattern writing data or exposure image data stored in the storage apparatus 109. Detection data in units of the stripe region 32 (or in units of the irradiation region 34) for which individual distortion corrections for each of the grids 29 are finished is output to the enlarged distortion correcting circuit 142.

Figure 11:
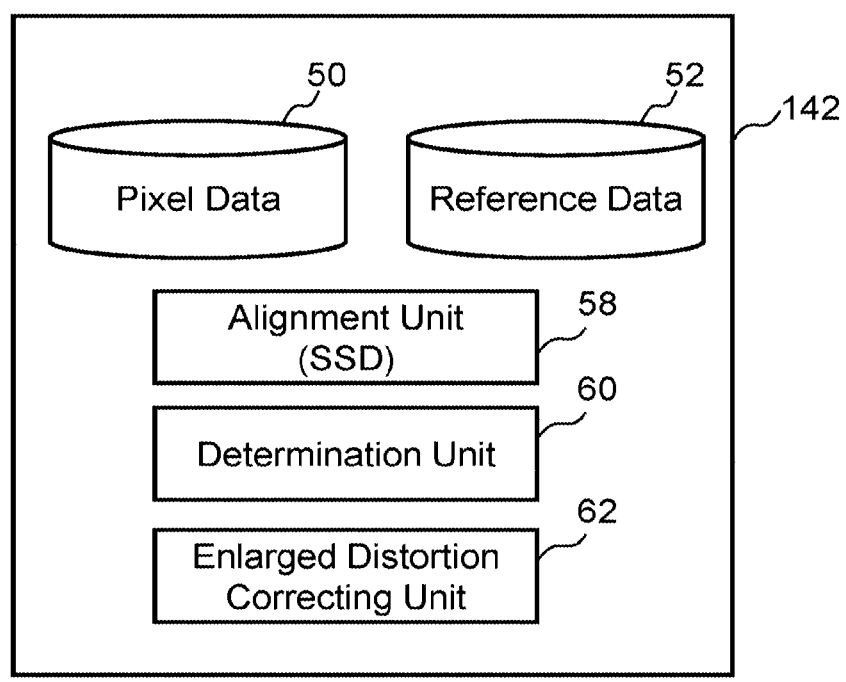
FIG. 11 is a diagram showing an internal configuration of an enlarged distortion correcting circuit according to Embodiment 1.

FIG. 11 is a diagram showing an internal configuration of an enlarged distortion correcting circuit according to Embodiment 1; In FIG. 11, storage apparatuses 50, 52 such as magnetic disk drives, an alignment unit 58, a determination unit 60, and an enlarged distortion correcting unit 62 are arranged inside the enlarged distortion correcting circuit 142. Detection data (grid image) in units of the stripe region 32 (or in units of the irradiation region 34) for which individual distortion corrections for each of the grids 29 are finished is stored in the storage apparatus 50. In the storage apparatus 52, reference image data for each of the grids 29 is stored.

As the alignment process (S108), the alignment unit 58 reads a grid image for which individual distortion corrections are finished from the storage apparatus 50 and read the corresponding reference image from the storage apparatus 52. Then, a grid image for which individual distortion corrections are finished and the corresponding reference image are aligned using a predetermined algorithm for each of the grids 29. For example, the method of least squares (SSD method) is used for alignment. The alignment is suitably performed in units of a sub-pixel smaller than the pixel for measurement 36.

As the determination process (S110), the determination unit 60 determines whether there is any deviation from the reference image as a result of alignment in the alignment process (S108) for each of the grids 29. If a deviation arises in any of the grids 29 even if individual distortion corrections are finished, the process proceeds to the enlarged distortion correction process (S112). If a deviation arises in none of the grids 29 in unit of the stripe region 32 (or in units of the irradiation region 34), the process proceeds to the gradation correction (1) process (S114).

As the enlarged distortion correction process (S112), the enlarged distortion correcting unit 62 corrects distortion of a combined region image (second region image) in units of a combined region 37 (second region) larger than the grid 29 (first region) using data of each grid image (first region image) whose distortion is individually corrected for each beam of the multiple beams 20. As shown in FIG. 6, the $n_1 \times m_1$ grids 29 inside the irradiation region 34 are formed into groups of the $n_2 \times m_2$ neighboring grids 29 in the x and y directions (two-dimensionally). Then, one combined region 37(B) is formed for each group of the grouped $n_2 \times m_2$ neighboring grids 29.

Figure 12A:
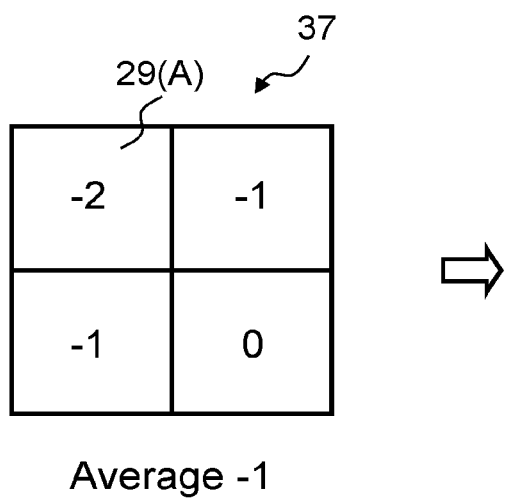
FIGS. 12A and 12B are diagrams illustrating how to make enlarged distortion corrections according to Embodiment 1.
Figure 12B:
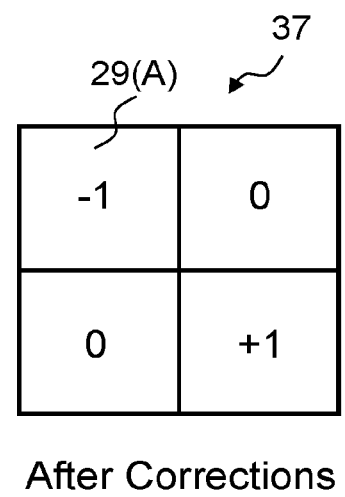

FIGS. 12A and 12B are diagrams illustrating how to make enlarged distortion corrections according to Embodiment 1; Examples of FIGS. 12A and 12B show a case in which the combined region 37 includes a group of the 2×2 neighboring grids 29 in the x and y directions (two-dimensionally). In FIG. 12A, an example of deviation amounts generated as a result of the alignment in the alignment process (S108) for each of the four grids 29 constituting a certain combined region 37 is shown. The example of FIG. 12A shows a case in which the distortion amount of the grid 29 on the upper left is "−2" nm, the distortion amount of the grid 29 on the upper right is "−1" nm, the distortion amount of the grid 29 on the lower left is "−1" nm, and the distortion amount of the grid 29 on the lower right is "0" nm. In the combined region 37, the average value of the distortion amount in the four grids 29 is "−1" nm. Thus, the enlarged distortion correcting unit 62 corrects the relevant combined region 37 such that the pattern positions inside the four grids 29 inside are each shifted by "+1 nm" obtained by inverting the sign of the average value. As a result, as shown in FIG. 12B, the distortion amounts of patterns inside the four grids 29 inside regarding the relevant combined region 37 are corrected to "−1" nm for the grid 29 on the upper left, "0" nm for the grid 29 on the upper right, "0" nm for the grid 29 on the lower left, and "+1" nm for the grid 29 on the lower right. Thus, the distortion amount can be made smaller by making corrections in units of the combined region 37 than a set of results of individual distortion corrections of the grids 29. Image data (pixel data) of each of the grids 29 on which enlarged distortion corrections have been made is output to the gradation correcting circuit 146.

As described above, a case in which a portion or all of patterns inside a portion or all of the grids 29 move into the neighboring grids 29 may arise by the pattern positions inside the grid 29 being moved (shifted) by individual or enlarged distortion corrections (or individual distortion corrections when individual distortion corrections are sufficient). Accordingly, the signal intensity changes (is corrected) from the pixel for measurement 36 to the pixel for measurement 36 inside the grid 29. Accordingly, when the gradation value in units of the grid 29 described below is calculated, a high-precision gradation value can be obtained.

Figure 13:
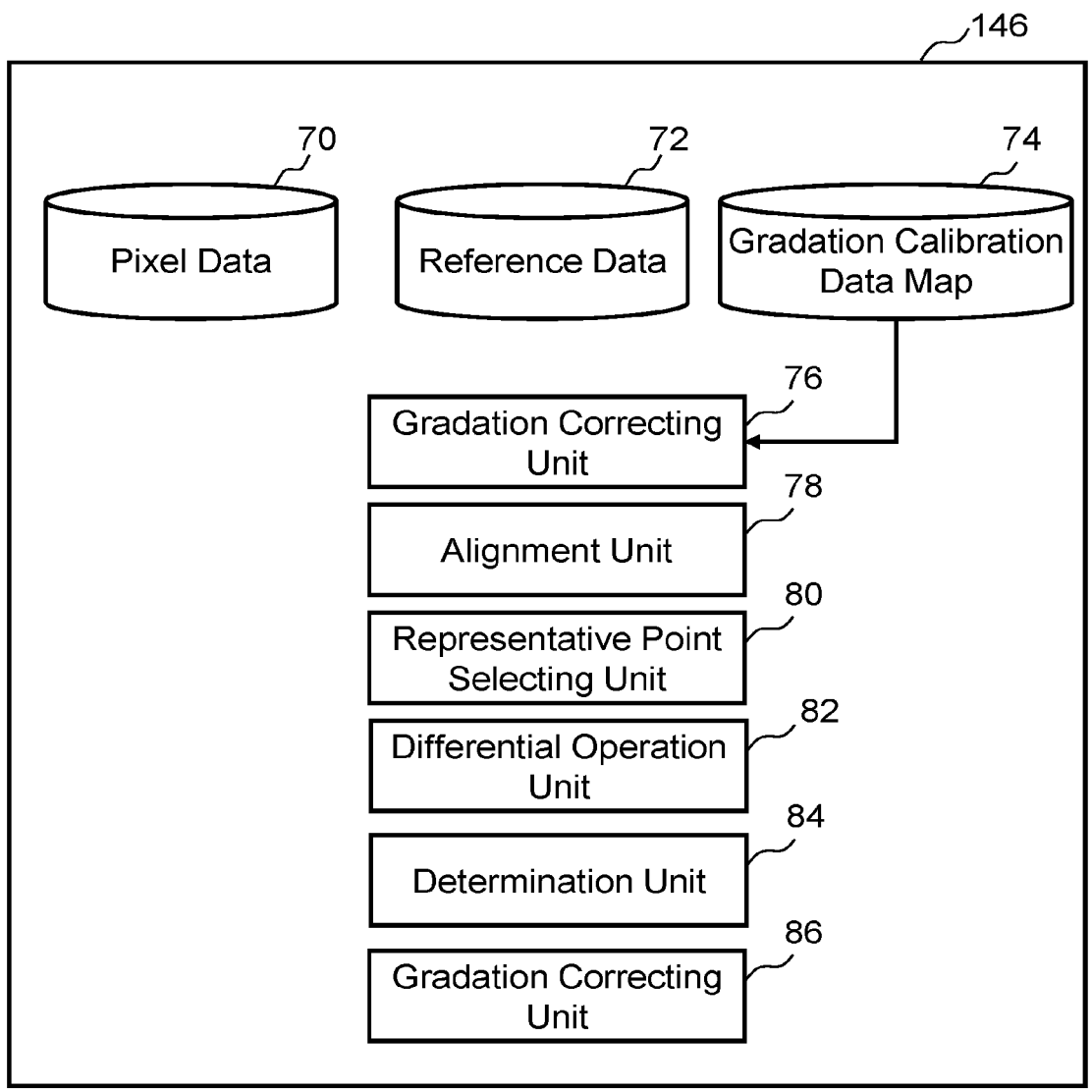
FIG. 13 is a diagram showing an internal configuration of a gradation correcting circuit according to Embodiment 1.

FIG. 13 is a diagram showing an internal configuration of a gradation correcting circuit according to Embodiment 1; and In FIG. 13, storage apparatuses 70, 72, 74 such as magnetic disk drives, a gradation correcting unit 76, an alignment unit 78, a representative point selecting unit 80, a differential operation unit 82, a determination unit 84, and a gradation correcting unit 86 are arranged inside the gradation correcting circuit 146. If a deviation arising in any of the grids 29 is determined in the determination process (S110), pixel data for which enlarged distortion corrections are made is stored in the storage apparatus 70. Alternatively, if a deviation arises in none of the grids 29 in unit of the stripe region 32 (or in units of the irradiation region 34) in the determination process (S110), pixel data for which individual distortion corrections are made is stored in the storage apparatus 70. Reference data of reference images is stored in the storage apparatus 72. Gradation correction data read by the control computer 110 from the storage apparatus 109 is stored in the storage apparatus 74.

As the gradation correction (1) process (S114), the gradation correcting unit 76 reads a grid image from the storage apparatus 70 in units of the combined region 37 to correct gradation errors of a combined region image (second region image) in units of the combined region 37 (second region). Also, the gradation value of a combined region image (second region image) is corrected using gradation values of a plurality of corresponding grid region images (third region images) obtained from sample regions of patterns of the same type.

Figures 14A, 14B, 14C:
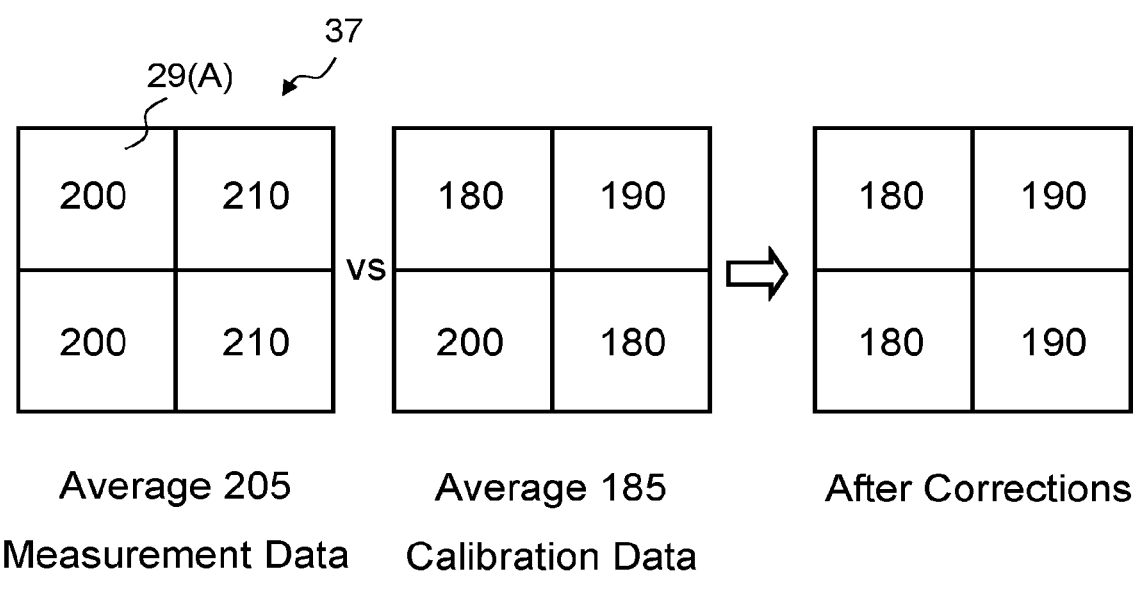
FIGS. 14A to 14C are diagrams illustrating how to make gradation corrections according to Embodiment 1.

FIGS. 14A to 14C are diagrams illustrating how to make gradation corrections according to Embodiment 1. Examples of FIGS. 14A to 14C show a case in which the combined region 37 includes a group of the 2×2 neighboring grids 29 in the x and y directions (two-dimensionally). In FIG. 14A, an example of gradation data after individual and/or enlarged distortion corrections for the four grids 29 constituting a certain combined region 37 is shown. The signal intensity of detection data (measurement data) after individual and/or enlarged distortion corrections maybe defined in 256 gradations for each of the pixels for measurement 36 to calculate the gradation value of the grid 29 as statistics of gradation values of a plurality of the pixels for measurement 36 inside the grid 29. For example, the average value, the minimum value, or the maximum value can be applied. However, the gradation value is not limited to 256 gradations. The example of FIG. 14A shows a case in which the gradation value of the grid 29 on the upper left is "200", the gradation value of the grid 29 on the upper right is "210", the gradation value of the grid 29 on the lower left is "200", and the gradation value of the grid 29 on the lower right is "210". The average value of the gradation values inside the combined region 37 is 205. FIG. 14B shows an example of the gradation values of grid images of the 2×2 corresponding grids 29 of gradation calibration data of the same pattern type measured in advance. The pattern type in the relevant grid 29 maybe determined using pattern writing data or exposure image data stored in the storage apparatus 109. The example of FIG. 14B shows a case in which the gradation value of the grid 29 on the upper left is "180", the gradation value of the grid 29 on the upper right is "190", the gradation value of the grid 29 on the lower left is "200", and the gradation value of the grid 29 on the lower right is "180". The average value of the gradation values of such gradation calibration data is 185. Thus, a differential value (gradation difference) obtained by subtracting the average value of the gradation value of the gradation calibration data from the average value of the gradation value of measurement data shown in FIG. 14A is "20". Thus, the gradation correcting unit 76 makes gradation corrections by subtracting the differential value (gradation difference) "20" from the gradation value of each of the grids 29 of the measurement data shown in FIG. 14A. As a result, as shown in FIG. 14C, the gradation value of each of the grids 29 of the measurement data after the corrections are corrected to "180" for the grid 29 on the upper left, "190" for the grid 29 on the upper right, "180" for the grid 29 on the lower left, and "190" for the grid 29 on the lower right. Thus, gradation errors can be made smaller by making corrections in units of the combined region 37.

As the alignment process (S116), the alignment unit 78 reads an irradiation region image in units of the irradiation region 34 from the storage apparatus 70 and reads the corresponding reference image from the storage apparatus 72. Then, an irradiation region image and the corresponding reference image are aligned using a predetermined algorithm for each of the irradiation regions 34. For example, the method of least squares (SSD method) is used for alignment. The alignment is suitably performed in units of the pixel for measurement 36 or a sub-pixel smaller than the pixel for measurement 36.

As the representative point setting process (S118), the representative point selecting unit 80 selects one combined region 37 from inside the irradiation region 34 for each of the irradiation regions 34. The method of selection may be random.

As the gradation difference operation process (S120), the differential operation unit 82 calculates a gradation value for each of the grids 29 in the combined region 37 selected as a representative point inside the irradiation region 34. The signal intensity of pixel data may be defined by 256 gradations for each of the pixels for measurement 36 to calculate the gradation value of the grid 29 as statistics of gradation values of a plurality of the pixels for measurement 36 inside the grid 29. For example, the average value, the minimum value, or the maximum value can be applied. However, the gradation value is not limited to 256 gradations. Similarly, the differential operation unit 82 calculates a gradation value for each of the grids 29 for the reference data corresponding to the combined region 37 selected as a representative point. Then, the differential operation unit 82 calculates a differential value (gradation difference) obtained by subtracting the gradation value of the reference image from the gradation value of the measured image for each of the grids 29.

As the determination process (S122), the determination unit 84 determines whether gradation differences of all the grids 29 in the combined region 37 selected by a representative point are smaller than a threshold value Th". If smaller than the threshold value Th", the process proceeds to the gradation correction (2) process (S126). If not smaller than the threshold value Th", the process proceeds to the representative point change process (S124). A value sufficiently smaller than a threshold value Th used for defect determination in the comparison process (S130) described below may be set as Th". For example, if the threshold Th is "30", the threshold Th" is set to "3".

As the representative point change process (S124), if gradation differences of all the grids 29 in the combined region 37 selected by a representative point are not smaller than the threshold value Th", the representative point selecting unit 80 re-selects a representative point to change to a different combined region 37. Then, after returning to the gradation difference operation process (S120), the determination process (S122) is repeated until gradation differences of all the grids 29 in the combined region 37 selected by a representative point are smaller than the threshold value Th". If gradation differences of all the grids 29 in the combined region 37 are not smaller than the threshold value Th", it is highly probable that a defective region is originally present in the combined region 37. Thus, it is better to directly proceed to the comparison process (S130). On the other hand, if gradation differences of all the grids 29 in the combined region 37 are smaller than the threshold value Th", it is highly probable that such gradation differences are not due to defects, but simply gradation errors. Thus, such errors are further corrected.

As the gradation correction (2) process (S126), if gradation differences of all the grids 29 in the combined region 37 selected by a representative point are smaller than the threshold value Th", the gradation correcting unit 86 corrects (offsets) gradation differences of all the grids 29 in the relevant irradiation region 34 by statistics of the gradation differences of each of the grids 29 in the selected combined region 37. As the statistics, for example, the average value, the minimum value, or the maximum value may be applied. By combining the gradation correction (1) process (S114) and the gradation correction (2) process (S126), correction residuals of corrections by the gradation correction (1) process (S114) can be corrected by the gradation correction (2) process (S126). Thus, gradation errors can be corrected with high precision. Data of each grid image for which the gradation correction (2) process (S126) is finished is output to the comparator 108.

As the comparison process (S130), the comparator 108 compares an inspection image in which distortion of a combined region image (second region image) has been corrected using a reference image of the same region as that of the inspection image. Then, the comparator 108 outputs a result thereof. More specifically, the comparator 108 aligns a measured image and a reference image in units of the irradiation region 34 and then, compares the measured image and the reference image in units of the grids 29. The comparator 108 compares both in units of the grids 29 according to predetermined determination conditions to determine whether, for example, there is any defect such as a shape defect. If, for example, the gradation value difference for each of the grids 29 is larger than a determination threshold Th, the comparator 108 determines that there is a defect. Then, the comparator 108 outputs a comparison result. The comparison result may be output from the storage apparatus 109, the monitor 117, the memory 118, or the printer 119.

According to Embodiment 1, as described above, distortion (and gradation errors) caused by multiple-beam inspection in pattern inspection using the multiple beams 20 based on an electron beam can be corrected with high precision. Thus, dummy defects specific to multiple-beam inspection can be reduced in pattern inspection using the multiple beams 20 based on an electron beam. Particularly, distortion corrections can be made with high precision not only by making distortion corrections of one beam image after another of each beam, but also by making distortion corrections in units of the combined region 37 regarding the irradiation region 34 of the multiple beams 20 as a whole. Further, gradation corrections can be made with high precision by making, after distortion corrections, gradation corrections in units of the combined region 37 regarding the irradiation region 34 of the multiple beams 20 as a whole. Further, gradation corrections can be made with still higher precision by correcting correction residuals of gradation errors.

In the description above, each ". . . circuit" and each ". . . unit" include processing circuitry and as the processing circuitry, an electric circuit, a computer, a processor, a circuit board, a quantum circuit, a semiconductor device or the like may be used. Also, each ". . . circuit" may use common processing circuitry (the same processing circuitry). Alternatively, each ". . . circuit" may use different processing circuitry (separate processing circuitry). Similarly, each". . . unit" may use common processing circuitry (the same processing circuitry). Alternatively, each ". . . unit" may use different processing circuitry (separate processing circuitry). A program causing a processor or the like to execute may be recorded in a record carrier body such as a magnetic disk drive, a magnetic tape device, FD, ROM (read-only memory) or the like. For example, the position circuit 107, the comparator 108, the pattern generation circuit 111, the reference circuit 112, the individual distortion correcting circuit 140, the enlarged distortion correcting circuit 142, the gradation correcting circuit 146 and the like may include at least one of the above circuits. Similarly, the alignment unit 58, the determination unit 60, the enlarged distortion correcting unit 62 and the like may include at least one of the above circuits.

In the foregoing, the embodiments have been described with reference to concrete examples. However, the present embodiment is not limited to the concrete examples.

Parts of the apparatus configuration, the control method, and the like which are not needed to be explained directly for the explanation of the present invention are not described. However, a necessary apparatus configuration and a necessary control method can be appropriately selected and used.

In addition, all pattern inspection methods and pattern inspection apparatuses which include the elements of the present invention and can be attained by appropriately changing in design by a person skilled in the art are included in the spirit and scope of the invention.

Additional advantages and modification will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A pattern inspection method comprising:
   scanning an inspection substrate, to be inspected, on which a plurality of figure patterns is formed, the inspection substrate being scanned using multiple beams, where a plurality of electron beams is arranged with a predetermined pitch in the multiple beams, to detect a secondary electron group including reflected electrons emitted from the inspection substrate due to irradiation with the multiple beams;
   correcting individually distortion of each of a plurality of first region images each obtained from a detection signal of secondary electrons emitted from a corresponding first region of a plurality of first regions on the inspection substrate, the plurality of first regions each scanned by a corresponding beam of the multiple beams, for each beam of the multiple beams, and each of the plurality of first regions having a same first region size;
   correcting distortion of each of a plurality of second region images corresponding to a plurality of second regions each larger than the first region size using data of each of the plurality of first region images in which the distortion has been corrected individually for the each beam; and
   comparing an inspection image of a plurality of inspection images to be inspected, each inspection image being composed of the plurality of second region images in which the distortion been corrected, with a reference image of a same region as that of the inspection image to output a result thereof.

2. The method according to claim 1, further comprising: correcting gradation errors of the second region image in units of the second region.

3. The method according to claim 2, wherein the gradation errors are corrected after the distortion of the first region image is individually corrected.

4. The method according to claim 2, wherein the gradation errors are corrected after the distortion of the second region image is corrected.

5. The method according to claim 1, further comprising:
   scanning a calibration substrate on which a calibration pattern is formed, the calibration substrate being scanned using the multiple beams, to detect secondary electron group including reflected electrons emitted from the calibration substrate due to irradiation with the multiple beams; and
   measuring a distortion amount of each of a plurality of third region images each obtained from a detection signal of secondary electrons emitted from a corresponding third region of a plurality of third regions on the calibration substrate, the plurality of third regions each having a same size as the first region size,
   wherein the first region image for the each beam is corrected using the distortion amount of the each of the plurality of third region images on the calibration substrate measured.

6. The method according to claim 1, further comprising:
   scanning a sample region for each pattern type of the plurality of figure patterns on the inspection substrate using the multiple beams to detect the secondary electron group including the reflected electrons emitted from the inspection substrate due to the irradiation with the multiple beams; and
   measuring individually a gradation value of a third region image obtained from a detection signal of secondary electrons corresponding to a third region in the sample region of a same size as the first region size, the third region being scanned by a beam of the multiple beams, for the each pattern type and the each beam of the multiple beams,
   wherein a gradation value of the second region image is corrected using the gradation values of a plurality of third region images obtained from the sample region of the same pattern type.

7. The method according to claim 1, further comprising:
aligning the inspection image of the plurality of inspection images with the reference image that corresponds to the inspection image, using a predetermined algorithm;
selecting one second region of the plurality of second regions as a representative point from inside the inspection image, for each of the plurality of inspection images;
determining whether a gradation difference of each first region between the inspection image and the reference image is smaller than a threshold value for all of the plurality of first regions inside the representative point selected; and
offsetting, when the gradation difference of the each first region is smaller than the threshold value for all the plurality of first regions in the second region selected as the representative point, the gradation values of all the first regions inside the inspection image by statistics of the gradation difference of each of the first regions in the second region selected.

8. The method according to claim 7, further comprising: re-selecting the representative point when the gradation difference of any one of the first regions in the second region selected as the representative point is not smaller than the threshold value.

9. The method according to claim 7, further comprising:
correcting gradation errors of the second region image in units of the second region,
wherein the alignment is performed after the gradation errors are corrected.

10. A pattern inspection apparatus comprising:
a movable stage on which an inspection substrate, to be inspected, on which a plurality of figures is formed, is placed;
an electron beam column configured to irradiate the inspection substrate with multiple beams in which a plurality of electron beams is arranged with a predetermined pitch;
a detector configured to scan the inspection substrate using the multiple beams and to detect a secondary electron group including reflected electrons emitted from the inspection substrate due to irradiation with the multiple beams;
first correction processing circuitry configured to correct individually distortion of each of a plurality of first region images each obtained from a detection signal of secondary electrons emitted from a corresponding first region of a plurality of first regions on the inspection substrate, the plurality of first regions each scanned by a corresponding beam of the multiple beams, for each beam of the multiple beams, and each of the plurality of first regions having a same first region size;
second correction processing circuitry configured to correct distortion of each of a plurality of second region images corresponding to a plurality of second regions each larger than the first region size, using data of each of the plurality of first region images in which the distortion has been corrected individually for the each beam; and
comparison processing circuitry configured to compare an inspection image of a plurality of inspection images to be inspected, each inspection image being composed of the plurality of second region images and in which the distortion has been corrected, with a reference image of a same region as that of the inspection image.

* * * * *